United States Patent
Freese

(10) Patent No.: US 10,952,856 B2
(45) Date of Patent: Mar. 23, 2021

(54) SPINAL FUSION CONTAINMENT SYSTEM

(71) Applicant: FreeseTEC Corporation, Exton, PA (US)

(72) Inventor: Andrew Freese, Chester Springs, PA (US)

(73) Assignee: FREESETEC CORPORATION, Exton, PA (US)

( * ) Notice: Subject to any disclaimer, the term of this patent is extended or adjusted under 35 U.S.C. 154(b) by 0 days.

(21) Appl. No.: 15/130,634

(22) Filed: Apr. 15, 2016

(65) Prior Publication Data
US 2016/0302929 A1 Oct. 20, 2016

Related U.S. Application Data

(60) Provisional application No. 62/253,959, filed on Nov. 11, 2015, provisional application No. 62/147,944, filed on Apr. 15, 2015.

(51) Int. Cl.
*A61B 17/70* (2006.01)
*A61F 2/28* (2006.01)
*A61F 2/46* (2006.01)

(52) U.S. Cl.
CPC ............ *A61F 2/2846* (2013.01); *A61B 17/70* (2013.01); *A61B 17/7043* (2013.01); *A61B 17/7049* (2013.01); *A61F 2/4601* (2013.01); *A61B 2017/7073* (2013.01); *A61F 2002/285* (2013.01)

(58) Field of Classification Search
CPC .......................... A61F 2/2846; A61B 17/7043
See application file for complete search history.

(56) References Cited

U.S. PATENT DOCUMENTS

| | | | | |
|---|---|---|---|---|
| 5,993,449 A | * | 11/1999 | Schlapfer | A61B 17/7059 606/60 |
| 7,806,911 B2 | * | 10/2010 | Peckham | A61B 17/7059 606/248 |
| 8,998,961 B1 | * | 4/2015 | Ziemek | A61B 17/705 606/260 |
| 9,526,533 B1 | * | 12/2016 | Aranibar | A61B 17/7067 |
| 2005/0177162 A1 | * | 8/2005 | McLeod | A61B 17/8028 606/70 |
| 2005/0261782 A1 | * | 11/2005 | Hoganson | A61F 2/0063 623/23.74 |
| 2006/0004358 A1 | * | 1/2006 | Serhan | A61B 17/70 606/281 |

(Continued)

*Primary Examiner* — Jan Christopher L Merene
(74) *Attorney, Agent, or Firm* — Pabst Patent Group LLP

(57) ABSTRACT

Bone graft retention devices, systems, and methods for retaining bone graft material at a desired site are described. The devices may attach to existing bone fusion systems or components thereof, such as rods or cross connectors, or may be integrated directly into a cross connector. The devices include a fin, and optionally one or more attachment elements. The bone graft material is attached to the fin, such as via an adhesive or by friction fit inside a cavity. Optionally, during insertion in a patient, the fin is flipped upwards so that it does not hinder the insertion. Following insertion of the rod or cross-connector in the desired location and tightening of the screws into their final positions, the fin of the bone graft retention device is flipped into place such that it aligns with the spine, pressing the bone graft material against the spine.

33 Claims, 10 Drawing Sheets

(56) References Cited

U.S. PATENT DOCUMENTS

| | | | |
|---|---|---|---|
| 2006/0276788 A1* | 12/2006 | Berry | A61B 17/7005 606/286 |
| 2007/0162122 A1* | 7/2007 | Whittaker | A61F 2/0811 623/13.14 |
| 2007/0162132 A1* | 7/2007 | Messerli | A61B 17/68 623/17.11 |
| 2007/0233091 A1* | 10/2007 | Naifeh | A61B 17/7005 606/279 |
| 2007/0270812 A1* | 11/2007 | Peckham | A61B 17/7059 606/279 |
| 2008/0015586 A1* | 1/2008 | Krishna | A61B 17/8028 606/86 A |
| 2009/0204092 A1* | 8/2009 | Loyd | A61F 13/472 604/385.03 |
| 2009/0299411 A1* | 12/2009 | Laskowitz | A61B 17/7008 606/246 |
| 2009/0326589 A1* | 12/2009 | Lemoine | A61B 17/7064 606/280 |
| 2010/0049252 A1* | 2/2010 | Smisson, III | A61B 17/7043 606/250 |
| 2010/0174315 A1* | 7/2010 | Scodary | A61B 17/7043 606/248 |
| 2010/0280552 A1* | 11/2010 | Lee | A61B 17/705 606/250 |
| 2011/0264229 A1* | 10/2011 | Donner | A61F 2/30988 623/18.11 |
| 2012/0095512 A1* | 4/2012 | Nihalani | A61B 17/7004 606/251 |
| 2012/0150230 A1* | 6/2012 | Felix | A61B 17/7049 606/250 |
| 2014/0018858 A1* | 1/2014 | Laeng | A61B 17/7002 606/270 |
| 2014/0249584 A1* | 9/2014 | Seex | A61B 17/7043 606/279 |
| 2014/0277154 A1* | 9/2014 | Perry | A61B 17/7044 606/270 |
| 2016/0135846 A1* | 5/2016 | Mirda | A61B 17/7004 606/267 |
| 2016/0302929 A1* | 10/2016 | Freese | A61F 2/2846 |
| 2016/0324642 A1* | 11/2016 | Maria de Peppo | A61K 35/12 |
| 2017/0056164 A1* | 3/2017 | Wang | A61F 2/2418 |
| 2017/0151065 A1* | 6/2017 | Warren | A61F 2/4425 |
| 2017/0202645 A1* | 7/2017 | Malinin | A61C 8/0006 |
| 2017/0216033 A1* | 8/2017 | Daniel | A61F 2/2846 623/17.17 |
| 2017/0238971 A1* | 8/2017 | Roger | A61B 17/7043 |
| 2017/0239050 A1* | 8/2017 | Vickers | A61F 2/2846 |
| 2017/0239051 A1* | 8/2017 | Engman | A61F 2/2846 |

* cited by examiner

SPINAL FUSION CONTAINMENT SYSTEM

CROSS-REFERENCE TO RELATED APPLICATION

The present application claims priority to U.S. Provisional Application No. 62/253,959, filed on Nov. 11, 2015 and U.S. Provisional Application No. 62/147,944, filed Apr. 15, 2016, by Andrew Freese, the disclosures of which are incorporated herein by reference in their entirety.

FIELD OF THE INVENTION

The invention is generally directed to spinal fusion devices and methods of use thereof.

BACKGROUND OF THE INVENTION

Each year, several hundred thousand spinal fusions are performed in the United States, and over one million a year in the world. While performing spinal fusion surgery, such as posterolateral fusion, surgeons often place screws through the posterior spine into the pedicles or lamina/lateral masses. These screws are connected with rods and secured in place to immobilize the spine. Then, bone graft or bone graft substitutes, such as VITOSS® (Stryker Corp.) or INFUSE® (Medtronic), are placed lateral to the combined screws and rods to induce bony fusion and bone formation across the affected spinal elements. For example, a bone bridge may form between the transverse processes of the spine. Currently, the bone formation inducing material, i.e. a bone graft or bone graft substitute, is placed freely along and between the transverse processes, sacral alae, and/or lateral masses of the spine.

Unfortunately nothing is done to ensure that the bone graft or bone graft substitute remains in place, and often the graft material dislodges, resulting in suboptimal fusion results.

Postoperative radiology reports often indicate that the position and location of the bone that is formed due to application of the bone graft or bone graft substitute is not where it was expected, indicating the bone formation inducing material migrated out of the site of its initial placement, which can lead to ectopic bone formation. These observations lead to significant concern and poor outcomes from fusion surgery. The compressed bone or bone substitute can compress or irritate neural structures, such as nerves or the spinal cord.

There is a need for improved methods and devices for preventing the movement of bone graft material after it is implanted.

Therefore it is an object of the invention to provide devices for maintaining the location of a bone graft material following implantation.

It is a further object of the invention to provide devices and systems for preventing a bone graft material from dislodging from the initial site of application in a patient's body.

It is yet a further object of the invention to provide methods for enhancing bone fusion and/or for preventing a bone graft material from dislodging from the initial site of application in a patient's body.

It is a still further object of the invention to provide an improved multi-axial cross connector.

SUMMARY OF THE INVENTION

Bone graft retention devices and methods for containing bone graft or bone graft substitutes (herein collectively referred to as "bone graft material") to prevent them from dislodging from the initial site of application in a patient's body are described herein. The bone graft retention devices may attach to spinal fusion systems or components thereof, such as pedicle screws, rods or cross connectors. Typically, they are attached after implantation of these systems or components. Alternatively, the bone graft retention device may be integrated directly into a spinal fusion device, such as a cross connector. In some embodiments, the bone graft material is attached to the bone graft retention device by friction fitting it in a pocket in the device. Alternatively, the bone graft material is attached to the bone graft retention device via a suitable adhesive material.

A cross connector that contains two components can pivot relative to each other to achieve the necessary positioning of the two components is also described herein. The cross connector preferably includes one or more attachment elements configured to receive mating portions of the fin of a bone graft retention device.

BRIEF DESCRIPTION OF THE DRAWINGS

FIG. 1A is a top view of the device; FIG. 1B is a bottom view of the device.

FIG. 3A is a bottom view of the device; FIG. 3B is a lateral view of the device.

FIG. 5A is a top perspective view; FIG. 5B is a top view.

DETAILED DESCRIPTION OF THE INVENTION

Figure 1A:
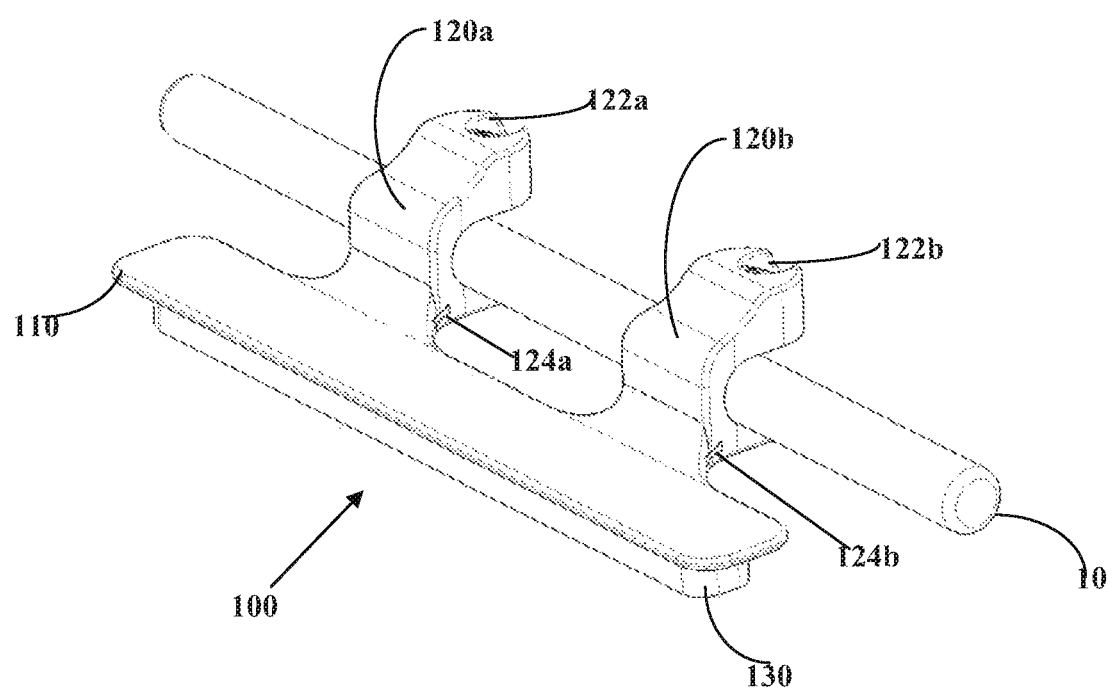
FIGS. 1A and 1B are two views of an exemplary bone graft retention device that is attached to a rod.

I. Bone Graft Retention Devices and Systems

The Bone graft retention devices 100 and systems contain an elongated portion, referred to herein as a "fin", which is configured to contain the bone graft material. The bone graft retention devices may attach to spinal fusion systems or components thereof, such as pedicle screws, rods, bone plates, hooks, or cross connectors.

In some embodiments, the fin contains one or more attachment portions on one side of the fin, which are configured to mate with and attach to one or more attachment elements or directly to a cross connector. Exemplary modular systems are depicted in FIGS. 1A, 1B, 2, 5A, 5B, 6, 8, and 9.

In other embodiments, the fin is integrated with the cross connector or the one or more attachment elements.

A. Fin i. Size and Shape

The fin 110 can have any suitable geometry. In the preferred embodiment, the fin is generally rectangular. See, e.g. FIG. 1A. The fin may be used in spinal fusions that fuse two or more discs or spinal segments together. The fin may have a suitable length to assist in one-level, two-level, or greater spinal fusions. The fin generally has a superior side 112 and an inferior side 113. The fin may contain a region for attachment, such as a pocket 140, typically on its inferior side 113, for receiving a bone graft material or bone graft substitute material. In some embodiments, a bone graft material or bone graft substitute material may be attached to the fin on one side, typically the inferior side 113 by an adhesive.

The geometry and dimensions of the fin are suitable to allow the fin to retain a sufficient volume of bone graft material. For example, for a fin used in a one-level fusion, the fin has suitable dimensions to retain approximately 1 $cm^3$ to 5 $cm^3$ volumes of bone graft material between two vertebrae. For a fin used in a two-level fusion, the fin has suitable dimensions to retain approximately 2 $cm^3$ to 10 $cm^3$ volumes of bone graft material between three vertebrae.

Figure 4:
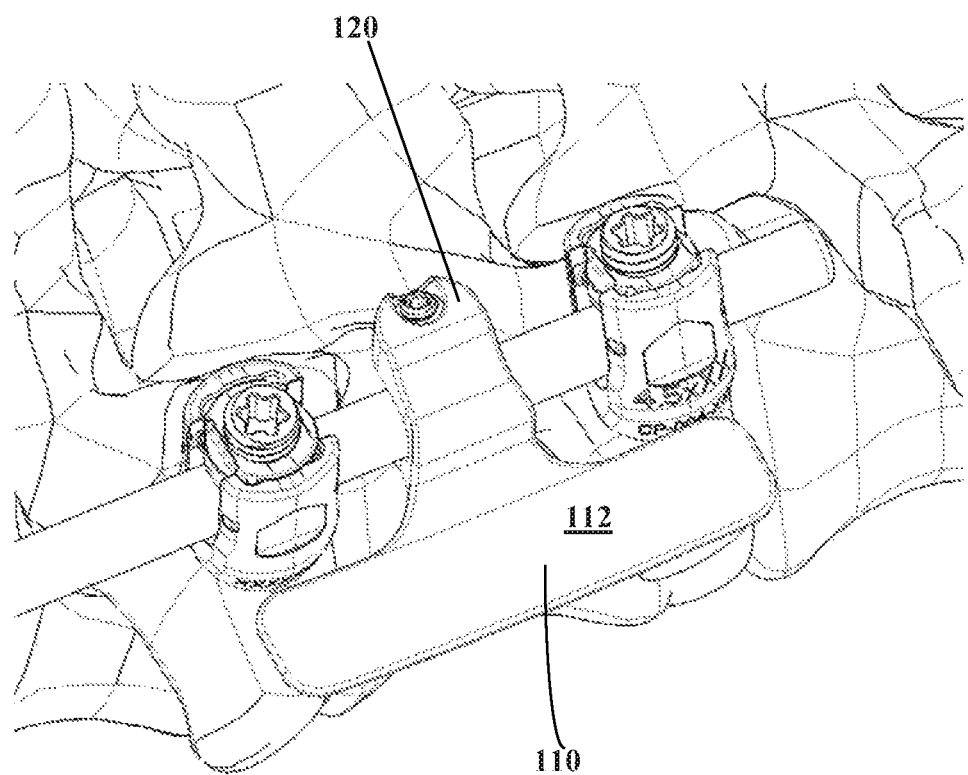
FIG. 4 is a top view of an exemplary bone graft retention device designed to assist in a one-level spinal fusion.

Suitable lengths range from 1 cm to 12 cm, or more for multiple level fusions. Preferred lengths are those that are suitable to assist in a one-level spinal fusion (see, e.g. FIG. 4), two-level spinal fusions (see, e.g., FIGS. 1A, 1B, 2, 3A, 3B, 5A, 5B, 6, 8, and 9), and multiple level fusions. For example, preferred lengths for use in a one-level fusion range from 1 cm to 6 cm; preferred lengths for use in a two-level fusion range from 2 cm to 12 cm.

Suitable widths range from 5 mm to 4 cm; and preferred widths range from 1 cm to 3 cm. Suitable widths for fins in a one-level, two-level, and multiple level spinal fusion are generally the same. Thickness of the fin can range from 1 mm to 1 cm.

The fin can be slightly curved such that it conforms to the natural curvature of the spine. For example for devices that are used in the lumbar and cervical regions of the spine, the fin has a suitable curvature to match the lordosis of the spine in these regions. See, e.g. FIG. 3B. Preferred angle for the curvature of the fin relative to the longitudinal axis of the spine is between 0° to 20°.

ii. Materials

The fin can be made out of any suitable biocompatible, non-degradable material with sufficient strength and rigidity to maintain its shape and support the bone graft material attached thereto. Optionally the fin is a continuous solid material. Alternatively, the fin can be formed from a mesh or a porous material.

Typical materials include biocompatible, non-biodegradable materials, such as polyaryletherketones (PAEKs), preferably poly(aryl-ether-ether-ketone) (PEEK) (e.g. PEEK-OPTIMA®, Invibio Inc), titanium or stainless steel. These materials are typically used in the hardware that is inserted into the spine.

Titanium is strong, lightweight, weighing 56% as much as steel, and it is one of the few materials that bone grows into and on. However, titanium, like all metals, has the drawback in that it is not translucent to X-rays or MRI scans. So once installed, it can blur or hide anatomical changes. But unlike steel, titanium is non-ferrous, so magnets used in MRI machines will not exert a force on them, and have been increasingly employed as biomaterials for orthopedic, trauma, and spinal devices.

PAEK is a family of high temperature thermoplastic polymers, consisting of an aromatic backbone molecular chain, interconnected by ketone and ether functional groups. These polymers are strong, inert, and biocompatible. Due to its strength and relative inertness, PEEK is broadly accepted as a radiolucent alternative to metallic biomaterials in the spine community.

The fin can be formed from a biodegradable material that remains intact for at least one month following implantation prior to biodegradation. Suitable biodegradable materials include but are not limited to polymeric materials containing polyhydroxy acids, such as polylactic acid, polyglycolic acid, and/or copolymers or blends thereof; polyanhydrides, and polyhydroxyalkanoates.

Biodegradable polymers for medical uses must degrade into non-toxic metabolites. Medical devices must also be nonpyrogenic, i.e., the products must not produce fever reactions when administered to patients. The presence of bacterial endotoxin (which is an integral component of the outer cell surface of Gram-negative bacteria) in the product is by far the largest concern of manufacturers in achieving nonpyrogenation. (Weary and Pearson, BioPharm., 1:22-29 (1988)). The U.S. Food and Drug Administration (FDA), for example, requires the endotoxin content of medical devices be less than 20 U.S. Pharmacopeia (USP) endotoxin fluid, where the content must not exceed 2.15 USP endotoxin units per device. U.S. Pat. No. 7,906,135 to Williams, et al. discloses polyhydroxy alkanoates (PHAs) from which pyrogen has been removed for use in numerous biomedical applications, including medical devices.

Representative synthetic polymers include but are not limited to poly(hydroxy acids) such as poly(lactic acid), poly(glycolic acid), and poly(lactic acid-co-glycolic acid), polyglycolides, polylactides, poly(lactide-co-glycolide) copolymers and blends, polyanhydrides, polyorthoesters, polyamides, polycarbonates, polyalkylenes such as polyethylene and polypropylene, polyalkylene glycols such as poly(ethylene glycol) (PEG), polyalkylene oxides such as poly(ethylene oxide) polyvinyl alcohols, poly(valeric acid), and poly(lactide-co-caprolactone), derivatives, copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxy acids such as lactic acid and glycolic acid, polylactide, polyglycolide, poly(lactide-co-glycolide), and copolymers with PEG, PHAs, polyanhydrides, poly(ortho)esters, polyurethanes, poly(butyric acid), poly(valeric acid), poly(lactide-co-caprolactone), blends and copolymers thereof.

Optionally, the fin contains a radiopaque marker to facilitate visualization via imaging.

B. Attachment Mechanism

The fin 110 is connected to a suitable attachment element 120a and 120b (collectively 120) configured for attaching the bone graft retention device to a spinal device, such as spinal fusion connector, pedicle screw, or portion thereof. Exemplary spinal fusion connectors include such as rods 10 and cross-connectors 200. In some embodiments, each attachment element 120 can have upper arm 127 and lower arm 128 (depicted in FIG. 1B as upper arms 127a and 127b and lower arms 128a and 128b). In some embodiments the fin is integral with the attachment element. In other embodiments, the fin is attachable to and removable from the attachment elements.

For example, the attachment mechanism can be a ball detent 122a and 122b (collectively 122) or a screw 126a and 126b (collectively 126) that can be tightened onto the connector. The ball detent allows for the bone graft retention device to snap onto any existing rod (such as a Ø5.5 mm rod) and rotate up and down.

Figure 2:
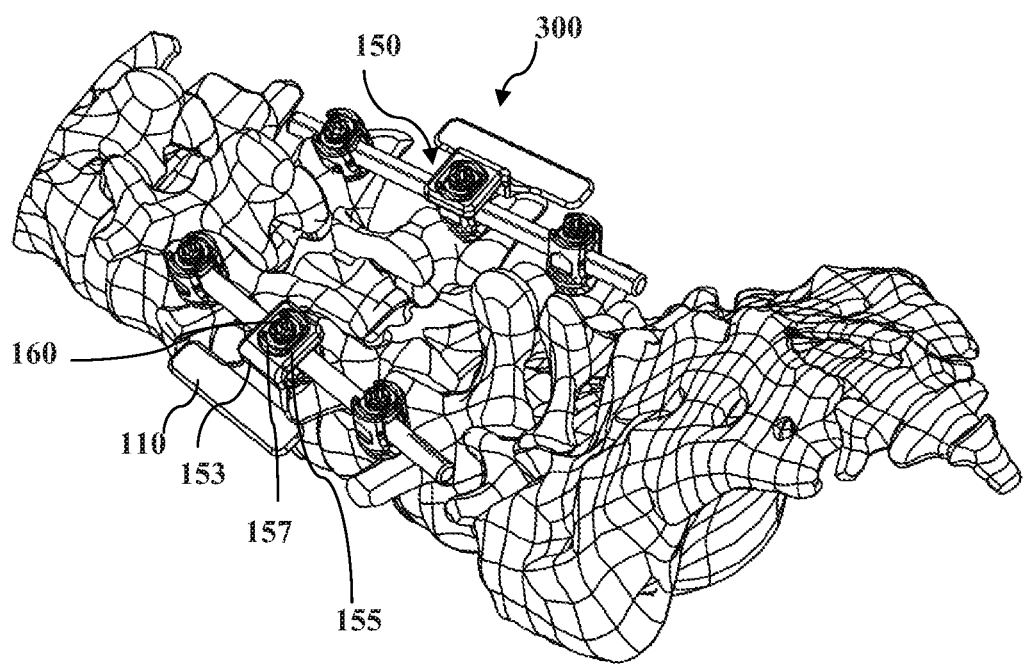
FIG. 2 is a top perspective view of an exemplary bone graft retention device attached to the head of a pedicle screw.
Figure 3A:
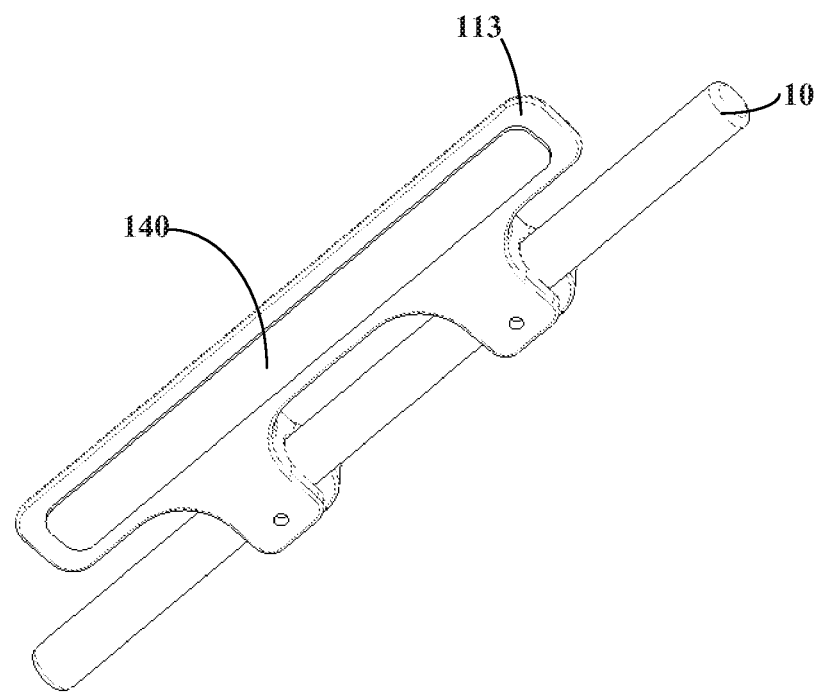
FIGS. 3A and 3B are two views of an exemplary bone graft retention device designed to assist in a two-level spinal fusion that is attached to a rod.
Figure 3B:
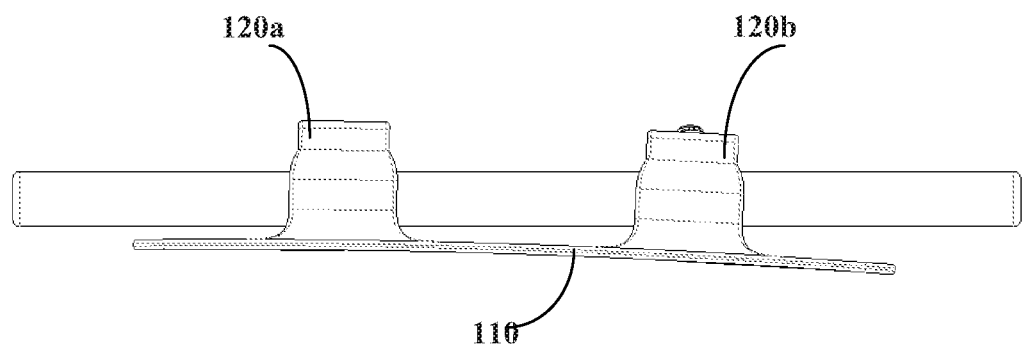

Another embodiment of the bone graft retention device is depicted in FIG. 2. The bone graft retention device 300 can be a singular device or have one or more attachment elements and detachable connectors forming a modular system. Here, the fin 110 is connected to an attachment element 150 configured for attaching the bone graft retention device to the head of a pedicle screw 160. The attachment element 150 has an upper arm 155 with at least one opening 157. The attachment element attaches to the head of the pedicle screw by any suitable system, including but not limited to friction fit, a rotational locking system, snap fit, etc. The opening 157 is has a suitable size and shape to receive the head of the pedicle screw assembly 160. The opening 157 is typically of a shape and a size that allows the head of the pedicle screw assembly 160 to fit snuggly inside the opening.

Other attachment means, such as a screw, could be used in place of the ball detent.

C. Detachable Connectors

Optionally the bone graft retention system is a modular system that contains one or more attachment elements and one or more fins, where the fins are configured to attach to at least one, and preferably two attachment elements. Each attachment element contains a slot or other suitable attachment means on one side to allow the fin to slide into and attach to the connector. Alternatively, the attachment means may mate with the fin to form a snap fit connection.

Figure 1B:
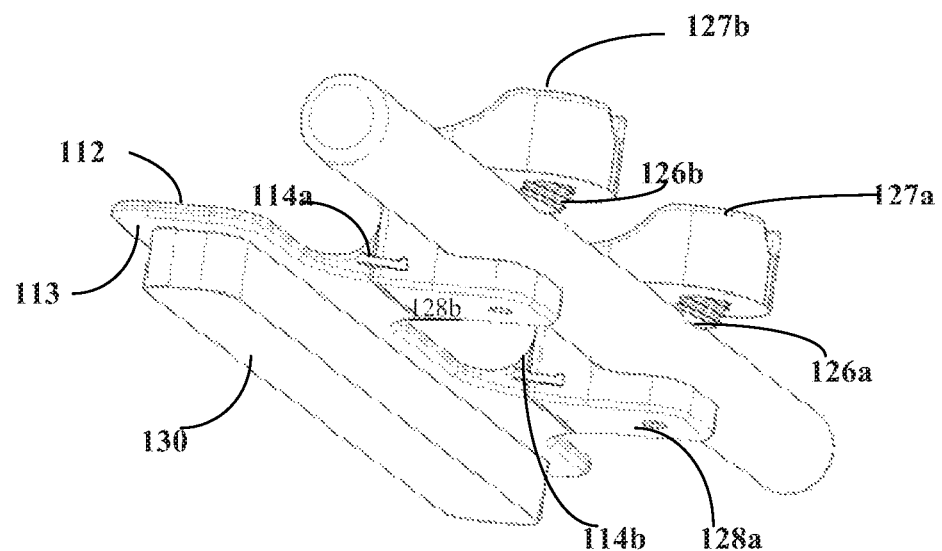
Figure 5A:
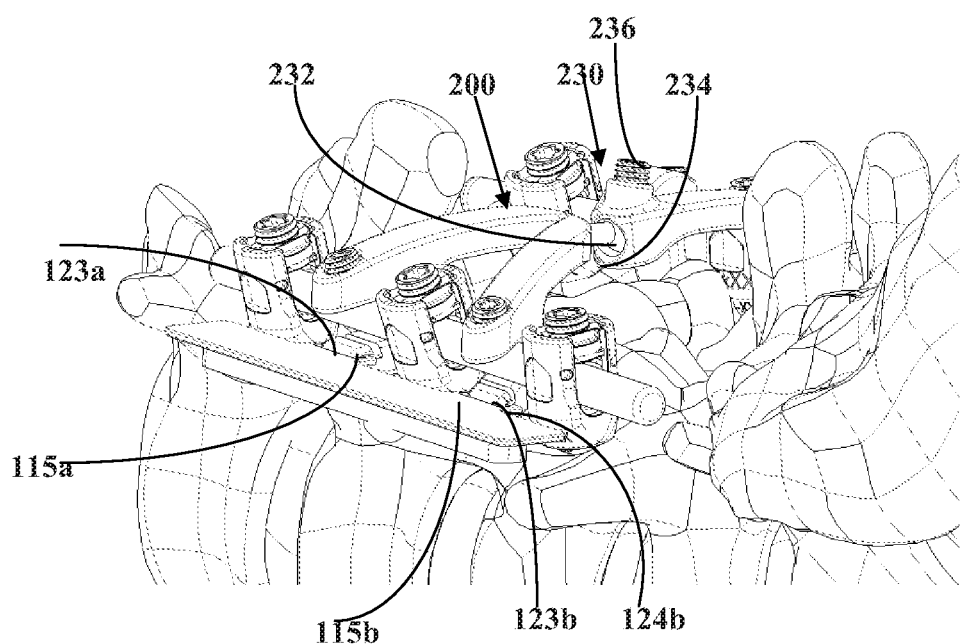
FIGS. 5A and 5B are two views of an exemplary bone graft retention device that is connected to a cross connector and implanted in a patient's spine.
Figure 5B:
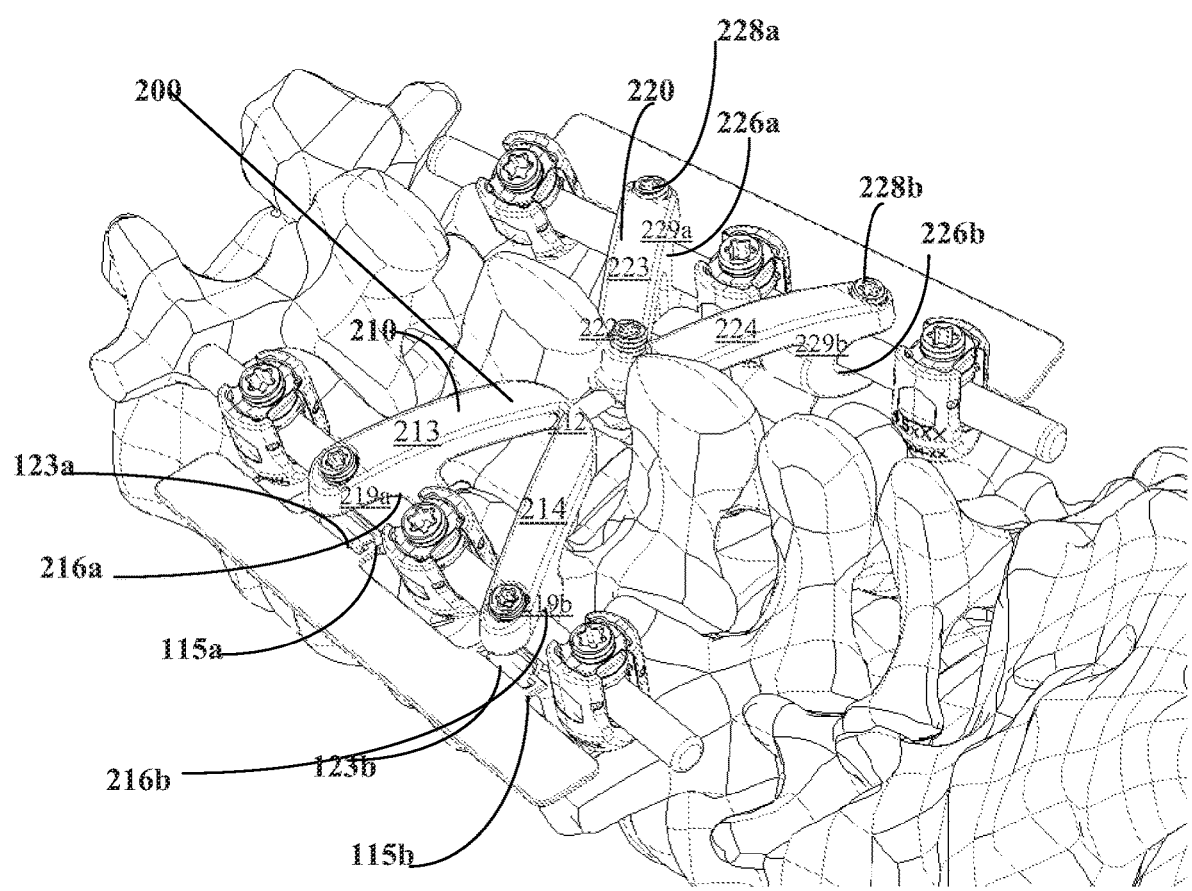

For example, as depicted in FIGS. 1A and 1B, each attachment element 120 contains a slot 124a and 124b (collectively 124) configured to receive an attachment portion 114a and 114b (collectively 114) of the fin that can slide into the slot. Alternatively, such as depicted in FIGS. 5A and 5B, each attachment element contains a hook 123a and 123b (collectively 123). Additionally, the attachment portion of the fin that connects with the hook is in the shape of a handle 115a and 115b (collectively 115) with a hollow central area (not visible in figure), such that the handle slips over the hook and is able to rest in a slot 124 in the attachment element. Other configurations for connecting the fin to the attachment element may be used in place of those described above.

In contrast, the attachment element 150 of the device 300 can be integral with the fin 110. In this embodiment, the attachment element may be added directly to a pedicle screw when the fin portion is needed, or omitted or removed from the pedicle screw system, if the fin portion is not needed.

D. Pocket for Bone Graft Material

The bone graft material 130 can be attached to the fin by any suitable means. Preferably the fin contains a region for attachment, such as a pocket 140. See, e.g. FIG. 3A. The pocket can be machined into the fin to fit the bone graft material. Alternatively, the bone graft material can be put in place over transverse processes or along the hardware. No attachment or pocket is required. The device can then be secured constraining the bone graft material.

i. Size and Shape

The pockets can range from 1 mm to 5 mm in depth, from 1 mm to 3.5 cm in width, and have variable lengths.

ii. Attachment of Bone Graft Material

The bone graft material can have any form, such as preformed implantable article, a paste, or flowable material that forms a gel at the site of application. Preferably the bone graft material is a preformed shaped article or strip, such as the VITOSS® Foam Strip or the VITOSS® Shapes. The bone graft can also be, for example, an autograft derived from the patient.

Optionally the bone graft material adheres to the fin via an adhesive. Suitable adhesives include cryanoacrylates, albumin and glutaraldehyde, fibrin glues, and polyethylene glycol based sealants. Alternatively, the bone graft material may have a suitable configuration to mate with a pocket and adhere to it via friction fit.

iii. Bone Graft Material

Any known bone graft or bone graft substitute may be used with the devices and systems described herein. Suitable bone graft or bone graft substitute materials are known to those skilled in the art.

A variety of materials may serve as bone grafts or bone graft substitutes, including autografts (harvested from the iliac crest of the patient's body), allografts, demineralized bone matrix (DBM), and various synthetic materials. The synthetic materials include calcium phosphates or hydroxyapatites, stem cell containing products which combine stem cells with one of the other classes of bone graft substitutes, and as the latest generation of bone graft substitutes, growth factor containing matrices, such as INFUSE® (rhBMP-2-containing bone graft) from Medtronic Sofamor Daniek, Inc.

Autograft is the gold standard because of efficacy and safety. Iliac Crest Bone Graft (ICBG) has a Calcium Phosphate (CaP) surface with an open porous structure. However, due to limited supply of a patient's own bone, the risk of donor site pain and morbidity (blood loss, infection) in combination with long hospital stays and operation time, there has been a continued search for bone graft substitutes to replace autologous bone.

VITOSS® is composed of β-TCP (tricalcium phosphate). In use, VITOSS® is typically combined with autologous bone marrow to induce bone formation.

Growth factor containing matrices, for example, INFUSE®, have demonstrated equivalent fusion rates to autograft and have therefore had significant impact on the market. INFUSE® contains a collagen matrix and BMP (bone morphogenetic protein). BMP is delivered to the patient from the matrix in high concentration.

Optionally the bone graft substitute contains one or more bioactive factors. Suitable bioactive factors include molecules, peptides and proteins having the capabilities of triggering regeneration of bone tissue. The bioactive factor is preferably PTH, a BMP, or a member of the TGF-beta superfamily. The parathyroid hormone can be PTH1-84 (native), $PTH_{1-38}$, $PTH_{1-34}$, $PTH_{1-31}$, $PTH_{1-28}$ or $PTH_{1-25}$, or any modified or allelic versions of PTH having the capabilities of triggering regeneration of bone tissue, or BMPB2 or BMP7.

There are at least 20 structurally and functionally related BMPs and several TGF βs, which are members of the TGF-beta superfamily. BMPs were originally identified as protein regulators of cartilage and bone formation. They are also involved in embryogenesis and morphogenesis of various tissues and organs. BMPs regulate the growth, differentiation, chemotaxis and apoptosis of various cell types, including mesenchymal cells, epithelial cells, hematopoietic cells and neuronal cells. Similar to other TGF-beta family proteins, BMPs are highly conserved across animal species.

Bone morphogenetic proteins 2 and 7 (BMP 2 and 7) are of specific interest in bone or cartilage formation applications. BMP 2 induces the formation of both cartilage and bone. The protein is synthesized as a prepropeptide. Full length human prepropetide BMP 2 is a glycosylated polypeptide having a sequence of 396 amino acids, consisting of a 19 amino acid signal sequence, a 263 amino acid pro region and a 114 amino acid mature segment. Cleavage of the pro-region occurs prior to segregation. The mature form has 7 cysteine moieties and one N-linked glycosylation site. The functional form of the protein consists of two disulfide-linked mature chains. It has been found that BMP 2 variants consisting only of a part of the mature amino acid sequence of BMP 2, such as the amino acids 283 to 396, also exhibit biological activity.

Human BMP 7, or osteogenic protein-1 (Op-1), is a 49 kDa, 431 amino acid preproprotein that is cleaved, similarly to BMP 2, into a 292 amino acid preproregion and a 139 amino acid mature segment. The mature segment contains three potential N-linked glycosylation sites plus seven cysteine residues.

Optionally, the bone graft or bone graft substitute material contains a radiopaque marker to facilitate visualization during imaging.

E. Modifications to Existing Devices

Existing spinal fusion devices may be modified to facilitate attachment of bone graft retention devices.

i. Spinal Rods

Figure 6:
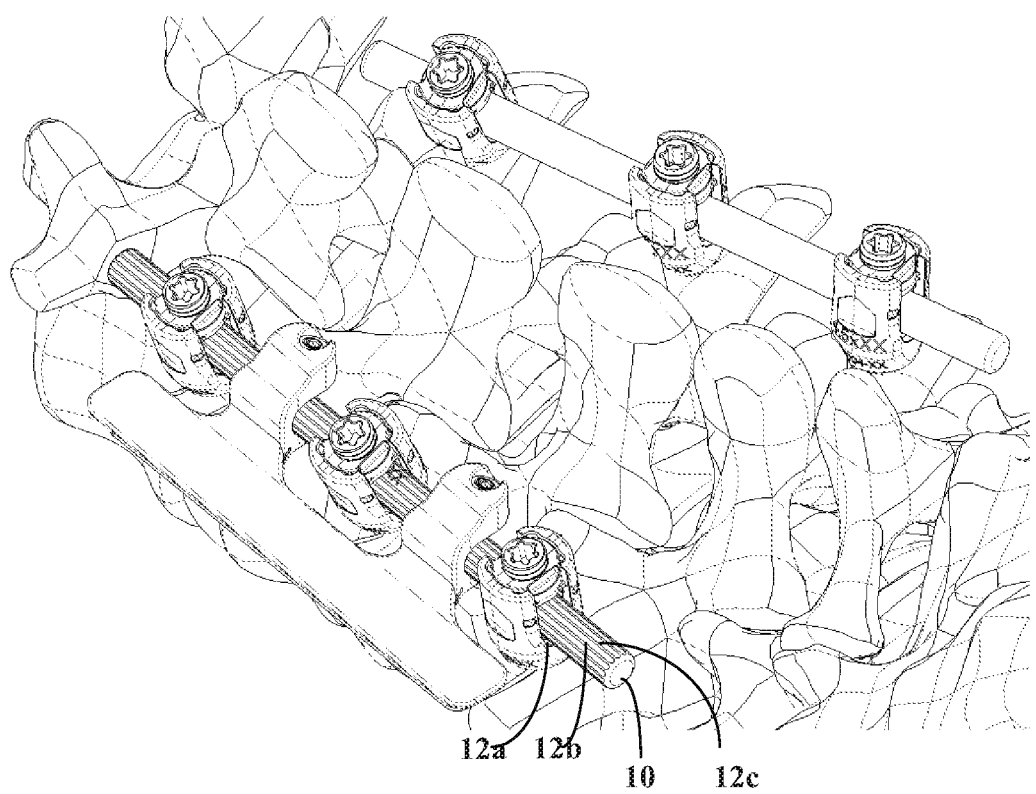
FIG. 6 is an illustration of an exemplary bone graft retention device that is implanted in a patient's spine, where the retention device is attached to a rod that is connected to three pedicle screws for a two-level spine fusion. As shown in this drawing, the rod has been modified to facilitate retention of the bone graft retention device.

For example, grooves may be machined on a rod to increase the connection between the attachment element and the surface of the spinal rod. As shown in FIG. 6, the rod 10 contains a plurality of grooves 12a, 12b, and 12c (collectively 12) within which the distal tip of the attachment element (e.g., the ball in a ball detent, or a screw) can rest. Additional force is needed to move the tip of the screw or ball out of the groove than is required to move a tip that is in contact with the smooth surface of a spinal rod.

ii. Cross Connectors

Spinal cross-connectors are typically attached at one or more points between the two spinal fixation rods in order to provide additional stability to the structure. Cross-connectors can be modified to include one or more connection elements, such as located on a clamp that affixes to a spinal rod.

One exemplary embodiment of a cross connector that contains a connection element for attachment of a bone graft retention device is depicted in FIGS. 5A and 5B. The cross connector assembly 200 is formed by connecting two elements 210 and 220 with an engagement mechanism 230 that provides a multiple degree of freedom articulation (e.g. pivoting) between the two elements. As shown in FIGS. 5A and 5B, the engagement mechanism contains a ball 232, which is located at the distal end 212 of one element, e.g. 210; and a socket 234, which is located at the distal end 222 of the other element, e.g. 220. The socket and ball have suitable sizes and shapes such that the ball fits inside the socket and can rotate therein. The engagement mechanism also includes a set screw 236, which can be tightened until it contacts the ball 232 and thereby prevents the first and second elements from rotating and fixes the relative locations of the first and second elements.

Each of the first and second elements contains two arms 213, 214 and 223, 224 that form a "V", and which meet at the distal end 212, 222. At the opposite end 219a, 219b and 229a, 229b (referred to herein as the "engagement end") each of the arms is configured to engage a spinal fusion device, such as a spinal rod. At the engagement end, each arm contains a curved opening 216a, 216b and 226a, 226b, configured to partially surround a rod or other portion of a spinal fusion device, a set screw bore (not visible in FIGS. 5A and 5B) and a set screw 228a, 228b for contacting and locking the arm into position on the spinal rod. Alternatively, either or both of the engagement ends may be configured to engage a different spinal fixation device, such as a bone plate, bone screw, or hook. Similarly, alternative means for fixing the engagement end to a spinal fusion device, such as a spinal rod, may be used in place of the configuration for the engagement ends depicted in FIGS. 5A and 5B.

Figure 8:
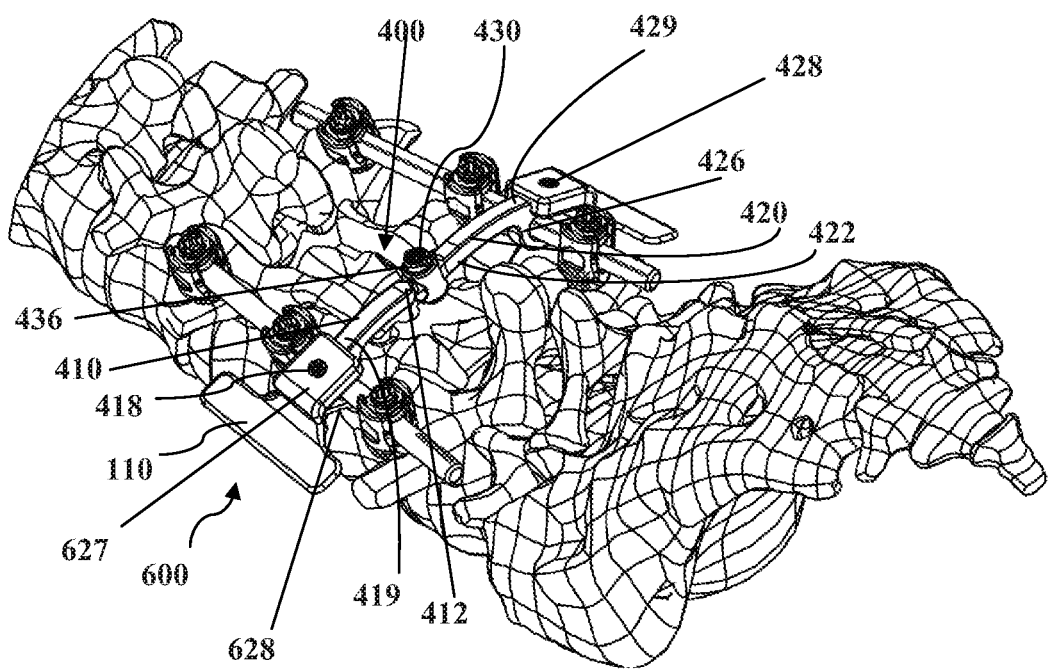
FIG. 8 is a top perspective view of an exemplary bone graft retention device attached to an exemplary cross connector and implanted in a patient's spine.
Figure 9:
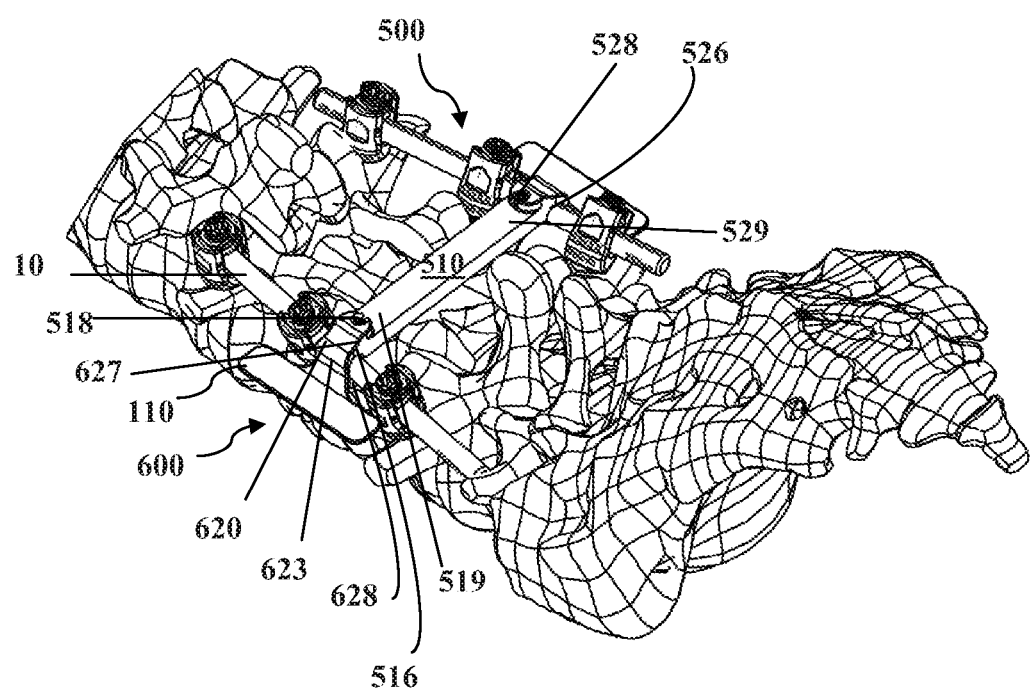
FIG. 9 is a top perspective view of an exemplary bone graft retention device attached to another exemplary cross connector and implanted in a patient's spine.

Other exemplary embodiments of a cross connector that contains a connection element for attachment of a bone graft retention device are depicted in FIGS. 8 and 9. In FIG. 8, the cross connector assembly 400 is formed by connecting two elements 410 and 420 with an engagement mechanism 430 that provides a multiple degree of freedom articulation (e.g. pivoting) between the two elements. The engagement mechanism 430 contains a set screw 436, which can be tightened until it contacts the distal end 412 of the first element 410 and thereby fixes the relative locations of the first and second elements. The distal end of the first element and the distal end of the second element may pivot relative to the engagement mechanism if the set screw is loose or absent from the engagement mechanism. After the first and second elements are in the desired positions, then the set screw is tightened to prevent them from moving out of these positions.

At the opposite ends (referred to herein as the "engagement ends") 419 and 429, each element of the cross connector is configured to engage a spinal fusion device, such as a spinal rod, and a bone graft retention device, such as device 600. At the engagement end, each element contains a curved opening, configured to partially surround a rod or other portion of a spinal fusion device, a set screw bore (not visible in FIG. 8) and set screws 418 and 428 for contacting and locking the respective arm into position on the spinal rod and the bone retention device.

Another exemplary embodiment of a cross connector for attaching a bone graft retention device to a spinal rod is depicted in FIG. 9. The solid cross connector assembly 500 is formed of a single element 510 with two ends 519 and 529.

At each of the opposite ends (referred to herein as the "engagement ends") 519 and 529, the solid cross connector is configured to engage a spinal fusion device, such as a spinal rod 10, and a bone graft retention device, such as device 600. Each of the engagement ends contains a curved opening 516 and 526, configured to partially surround a rod or other portion of a spinal fusion device, a set screw bore (not visible in FIG. 9) and a set screw 518 and 528 for contacting and locking the solid cross connector into position on the spinal rod and the bone retention device.

The device 600 is similar to device 100, with a modified attachment element 620. Attachment element 620 is configured for attaching the bone graft retention device to a spinal fusion connector, such as the rod 10, and the upper surface of an engagement end of the cross connector element 510. The attachment element 620 can have an upper arm 627 and a lower arm 628 connected by vertical portion 623 (depicted in FIG. 9). The distance between the upper arm 627 and the lower arm 628 is configured to accommodate the diameter of the rod and the height of the engagement ends 519 or 529 of the solid cross connector 500. The upper arm 627 contains a screw bore (not shown in FIG. 9) for receiving a set screw, such as the set screw 528 of the solid cross connector 500.

In some embodiments the fin 110 is integral with the attachment element. In other embodiments, the fin 110 is attachable to and removable from the attachment elements as described above. For example, the attachment element 620 of the device 600 can attach to the fin 110 by fitting the attachment portion 114 (FIG. 1B) into a slot (not visible in FIG. 9) on a vertical arm 623 of the attachment element 620 (FIG. 9).

The lengths of the arms in the first and second elements are sized to span a portion of the lateral distance between two spinal devices, such as spinal rods or implants, in a spinal fixation system.

Preferably, the engagement end of each arm also contains an attachment element 120 that is configured to receive an attachment portion of a fin 110. For example, each attachment element can contain a hook 123a and 123b. Additionally, the attachment portion of the fin that connects with the hook is in the shape of a handle 115a and 115b (collectively 115) with a hollow central area (not visible in figure), such that the handle slips over the hook and is able to rest in a slot 124 in the attachment element. Other configurations for connecting the fin to the attachment element may be used in place of those described above.

Additional cross connectors are known, such as those produced by Medtronic, DePuy-Synthes, Globus, Biomet, and Stryker. Existing cross connectors can be modified, such at their attachment ends, to include one or more attachment elements as described above. Alternatively, they can be modified to attach the fin directly to the cross connector, such as at its attachment portion, preferably in a manner that allows the fin to rotate (flip up and then down) to facilitate insertion in a patient's body.

II. Methods of Use

Figure 7A:
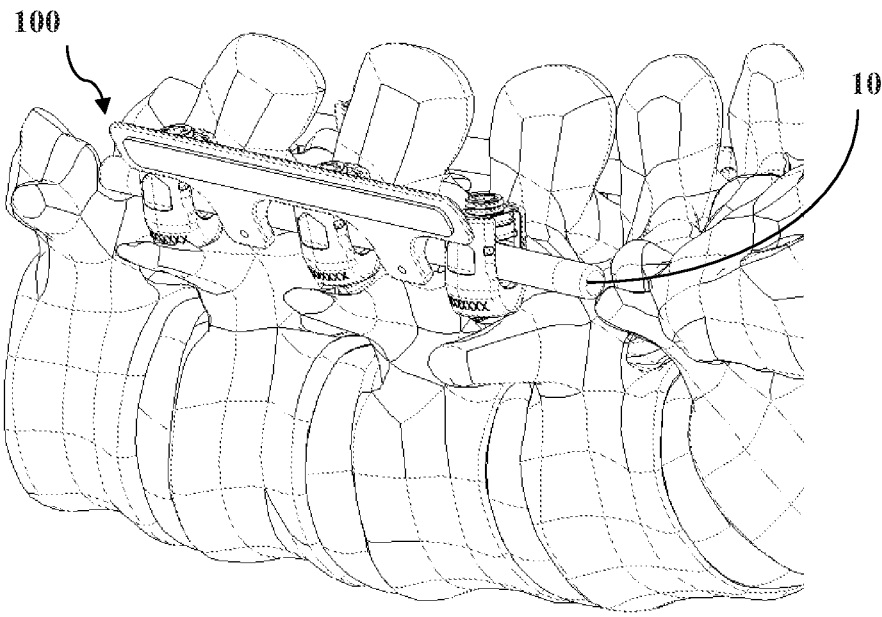
FIGS. 7A and 7B are illustrations of the relative position of the bone graft retention device when initially inserted into a patient's body (FIG. 7A); and when positioned in place to facilitate the spinal fusion (FIG. 7B).
Figure 7B:
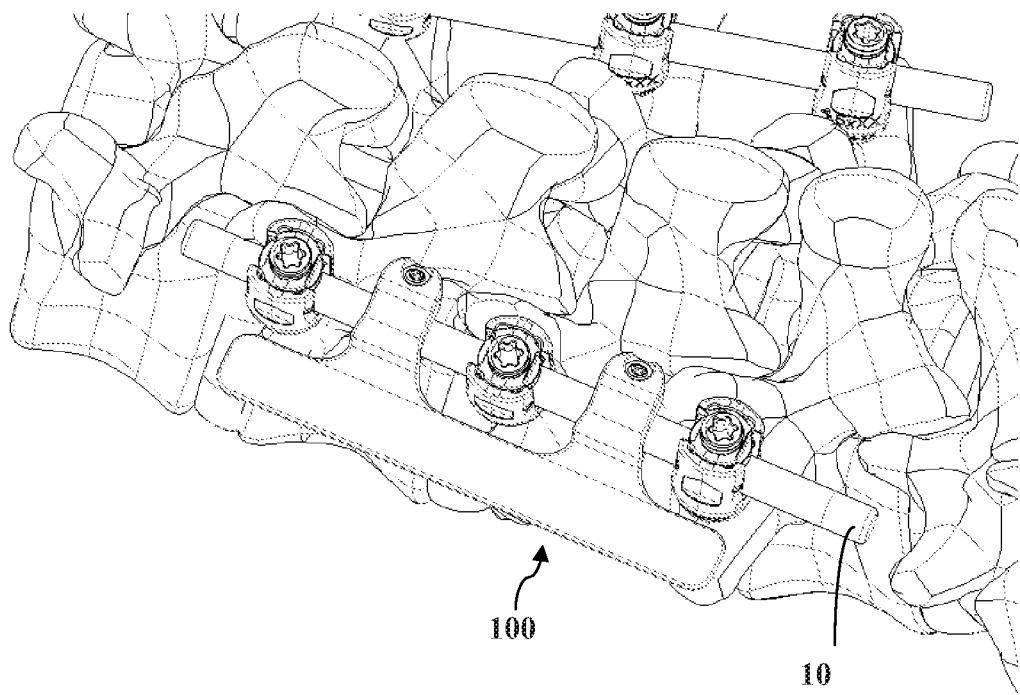

In use, optionally the bone graft retention device 100 is attached to a rod 10 or cross connector 200 prior to insertion into a patient's body. At the time of insertion, the fin of the bone graft retention device is flipped upwards so that it does not hinder the insertion. See FIG. 7A. Following insertion of the rod or cross-connector in the desired location and tightening of the screws into their final positions, the fin of the bone graft retention device is flipped into place such that it aligns with the spine (see FIG. 7B), thereby pressing the bone graft material against the spine, e.g. along and between the transverse processes, sacral alae, and/or lateral masses of the spine.

Alternatively, the bone graft retention device 100 may be inserted separately from the rod or cross connector, typically after the rod or cross connector is inserted into and positioned in the desired location (e.g. screws that fix it in place are tightened, as needed). Then the bone graft retention device 100 may be inserted into the patient and attached to the rod 10 or the cross connector 200.

A bone graft material or bone graft substitute material may be attached to the bone graft retention device at the time of insertion. Alternatively, the bone graft material or bone graft substitute material may be inserted into the patient before or after, typically after, the insertion of the bone graft retention device. In some embodiments, the bone graft material or bone graft substitute material is not attached to the fin, but it is constrained between the fin and the spine when the fin is in place (i.e. aligned with an abutting the spine).

I claim:

1. A bone graft retention device or system comprising an elongated fin, a bone graft material, and one or more attachment elements, wherein each attachment element comprises a set screw or a ball detent and a central pocket for receiving a rod,
   wherein the fin is securely attached to the one or more attachment elements,
   wherein the fin protrudes laterally beyond the one or more attachment elements,
   wherein the fin extends longitudinally from a first end to a second end, the fin comprises a superior surface opposite an inferior surface, the superior surface is substantially planar from the first end to the second end,
   wherein the inferior surface of the fin is configured to maintain the bone graft material along and between transverse processes, sacral alae, or lateral masses of the spine following implantation, and
   wherein the fin is a continuous solid material or a mesh material,
   wherein when the one or more attachment elements are attached to the rod, the ball detent or set screw bears down on the rod and the surface of the fin aligns approximately parallel with the rod,
   wherein following implantation, the rod is offset from the midpoint of spine, and the fin is offset from the midpoint of the spine and lateral from the rod.

2. The device or system of claim 1, wherein the fin comprises one or more attachment portions that mate with the one or more attachment elements to securely attach the fin to the one or more attachment elements.

3. The device or system of claim 1, wherein the fin is integral with the one or more attachment elements.

4. The device or system of claim 1, wherein the fin comprises a superior side and an inferior side, and wherein the fin comprises a pocket on its inferior side.

5. The device or system of claim 1, wherein the bone graft material is a porous solid having a preformed shape.

6. The device or system of claim 1, wherein the bone graft material is attached to the fin via an adhesive.

7. The device or system of claim 1, wherein the fin comprises a superior side and an inferior side, wherein the fin comprises a pocket on its inferior side, and wherein the bone graft material is attached to the pocket.

8. The device or system of claim 1, wherein the fin is able to rotate up and down relative to the one or more attachment elements when it is attached thereto.

9. The device or system of claim 1, wherein the one or more attachment elements comprises a set screw.

10. The device or system of claim 1, comprising more than one fin and more than one attachment element.

11. The device or system of claim 1, further comprising a cross connector, wherein the cross connector is configured to engage the fin and the rod,
wherein following implantation, the cross connector is attached to the rod and the fin.

12. The device or system of claim 11, wherein the cross connector comprises two elements that connect via an engagement mechanism, wherein each element comprises an engagement end that is configured to engage and attach to a spinal device, and wherein the engagement mechanism allows the elements to rotate relative to each other.

13. The device or system of claim 12, wherein the one or more attachment elements are attached to the engagement end of each element.

14. A spinal fusion method comprising,
(a) inserting into a site in the spine of a patient
a bone graft retention device or system comprising an elongated fin, a bone graft material, and one or more attachment elements, wherein each attachment element comprises a set screw or a ball detent and a central pocket for receiving a rod,
wherein the fin is securely attached to the one or more attachment elements,
wherein the fin protrudes laterally beyond the one or more attachment elements,
wherein the fin extends longitudinally from a first end to a second end, the fin comprises a superior surface opposite an inferior surface, the superior surface is substantially planar from the first end to the second end,
wherein the inferior surface of the fin is configured to maintain the bone graft material along and between transverse processes, sacral alae, or lateral masses of the spine following implantation, and
wherein the fin is a continuous solid material or a mesh material,
wherein when the one or more attachment elements are attached to the rod, the ball detent or set screw bears down on the rod and the surface of the fin aligns approximately parallel with the rod,
wherein following step (a), the rod is offset from the midpoint of spine, and the fin is offset from the midpoint of the spine and lateral from the rod.

15. The method of claim 14, wherein prior to step (a), a spinal fusion device is inserted into the site, and
wherein following step (a), the fin is attached to the spinal fusion device via the one or more attachment elements.

16. The method of claim 15 wherein the spinal fusion device is selected from the group consisting of rods, pedicle screws, bone plates, and cross connectors.

17. The method of claim 16, wherein the one or more attachment elements are attachable to and removable from the spinal fusion device.

18. The method of claim 16, wherein the fin of the device is flipped into a first upward position during step (a).

19. The method of claim 18, wherein following insertion, the fin is flipped downward such that the bone graft material abuts the spine.

20. The method of claim 15, wherein the bone graft material is constrained between the fin and the spine.

21. The device or system of claim 12, wherein each element comprises two arms that connect to each other and form a "V".

22. The device or system of claim 21, wherein the engagement mechanism further comprises a set screw configured to lock the engagement mechanism to prevent the elements from rotating.

23. A spinal fusion system comprising a rod, two or more pedicle screws, a bone graft material, and a bone graft retention device or system comprising an elongated fin and one or more attachment elements,
wherein each attachment element comprises a ball detent or a set screw and a central pocket for receiving the rod,
wherein the fin is securely attached to the one or more attachment elements, and wherein the fin protrudes laterally beyond the one or more attachment elements,
wherein the fin extends longitudinally from a first end to a second end, the fin comprises a superior surface opposite an inferior surface, the superior surface is substantially planar from the first end to the second end,
wherein the inferior surface of the fin is configured to maintain the bone graft material along and between transverse processes, sacral alae, or lateral masses of the spine following implantation, and
wherein the fin is a continuous solid material or a mesh material,
wherein when the one or more attachment elements are attached to the rod, the ball detent or set screw bears down on the rod, the surface of the fin aligns approximately parallel with the rod, and
wherein following implantation, the pedicle screws alternate with the one or more attachment elements, wherein one of the one or more attachment elements is located between two pedicle screws, the rod is offset from the midpoint of the spine, and the fin is offset from the midpoint of spine and lateral from the rod.

24. The spinal fusion system of claim 23, wherein the fin comprises one or more attachment portions that mate with the one or more attachment elements to securely attach the fin to the one or more attachment elements.

25. The spinal fusion system of claim 23, wherein the fin is integral with the one or more attachment elements.

26. The spinal fusion system of claim 23, wherein the fin comprises a superior side and an inferior side, and wherein the fin comprises a pocket on its inferior side.

27. The spinal fusion system of claim 23, wherein the bone graft material is a porous solid having a preformed shape.

28. The spinal fusion system of claim 23, wherein the bone graft material is attached to the fin via an adhesive.

29. The spinal fusion system of claim 23, wherein the fin is able to rotate up and down relative to the one or more attachment elements when it is attached thereto.

30. The spinal fusion system of claim 23, wherein the one or more attachment elements comprises a set screw.

31. The spinal fusion system of claim 23, comprising more than one attachment element.

32. The spinal fusion system of claim 23, further comprising a cross connector, wherein the cross connector comprises an engagement end configured to engage the fin and the rod,
wherein following implantation, the engagement end is attached to the rod and the fin.

33. A bone graft retention device or system comprising an elongated fin and one or more attachment elements, wherein each attachment element comprises a set screw or a ball detent and a central pocket for receiving a rod, wherein the fin is securely attached to the one or more attachment elements, wherein the fin protrudes laterally beyond the attachment elements, wherein the fin comprises a bone graft material attached thereto, wherein the fin extends longitudinally from a first end to a second end, the fin comprises a superior surface opposite an inferior surface, the superior surface is substantially planar from the first end to the second end, and wherein the inferior surface of the fin is configured to maintain the bone graft material along and between transverse processes, sacral alae, or lateral masses of the spine following implantation, and wherein when the one or more attachment elements are attached to the rod, the ball detent or set screw bears down on the rod and the surface of the fin aligns approximately parallel with the rod, wherein following implantation, the rod is offset from the midpoint of spine, and the fin is offset from the midpoint of the spine and lateral from the rod.

\* \* \* \* \*